(12) United States Patent
Maeda et al.

(10) Patent No.: US 11,701,138 B2
(45) Date of Patent: Jul. 18, 2023

(54) VIBRATION TRANSMITTER AND ULTRASONIC TREATMENT DEVICE

(71) Applicant: OLYMPUS CORPORATION, Tokyo (JP)

(72) Inventors: Yasuhiro Maeda, Hachioji (JP); Yukihiko Shimamura, Yoshikawa (JP); Masashi Yamada, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 604 days.

(21) Appl. No.: 16/900,269

(22) Filed: Jun. 12, 2020

(65) Prior Publication Data

US 2020/0305923 A1    Oct. 1, 2020

Related U.S. Application Data

(63) Continuation of application No. PCT/JP2017/044940, filed on Dec. 14, 2017.

(51) Int. Cl.
*A61B 17/00* (2006.01)
*A61B 17/32* (2006.01)

(52) U.S. Cl.
CPC ............. *A61B 17/320068* (2013.01); *A61B 2017/320032* (2013.01); *A61B 2017/320089* (2017.08); *A61B 2017/320094* (2017.08)

(58) Field of Classification Search
CPC .... A61B 17/320068; A61B 17/320092; A61B 2017/00477; A61B 2017/00526; A61B 2017/320032; A61B 2017/320089; A61B 2017/320094
See application file for complete search history.

(56) References Cited

U.S. PATENT DOCUMENTS

| | | | |
|---|---|---|---|
| 2014/0188144 A1 | 7/2014 | Taniguchi | |
| 2015/0018726 A1 | 1/2015 | Akagane | |
| 2017/0007854 A1* | 1/2017 | Yamada | ......... A61B 17/320068 |

FOREIGN PATENT DOCUMENTS

| | | | |
|---|---|---|---|
| CN | 103781432 A | 5/2014 | |
| JP | S57-076883 U | 5/1982 | |
| JP | S63-302842 A | 12/1988 | |
| JP | H03-296472 A | 12/1991 | |
| JP | 2005-094552 A | 4/2005 | |

(Continued)

OTHER PUBLICATIONS

Mar. 13, 2018 Search Report issued in International Patent Application No. PCT/JP2017/044940.

(Continued)

*Primary Examiner* — Mark D Remaly
(74) *Attorney, Agent, or Firm* — Oliff PLC

(57) ABSTRACT

A vibration transmitter includes: a first rod including a fitting hole extending along the longitudinal axis thereof; and a second rod attached to a distal end portion of the first rod by a fitting portion fitted into the fitting hole in a state where a compressed surface pressure is received from the inner surface of fitting hole. The first rod includes: a first region in which the fitting portion is fitted into the fitting hole; and a second region positioned proximal of the first region. In the first region of the first rod, a crystal grain diameter is larger than that in the second region of the first rod.

17 Claims, 9 Drawing Sheets

(56) References Cited

FOREIGN PATENT DOCUMENTS

| | | |
|---|---|---|
| JP | 2011-131342 A | 7/2011 |
| WO | 2014/038272 A1 | 3/2014 |
| WO | 2014/065177 A1 | 5/2014 |
| WO | 2016/203861 A1 | 12/2016 |

OTHER PUBLICATIONS

Jun. 16, 2020 English Translation of International Preliminary Report on Patentability issued in PCT Application No. PCT/JP2017/044940.
Nov. 9, 2022 Office Action issued in Chinese Patent Application No. 201780097686.2.
May 11, 2021 Office Action issued in Japanese Patent Application No. 2019-559501.

\* cited by examiner

VIBRATION TRANSMITTER AND ULTRASONIC TREATMENT DEVICE

CROSS-REFERENCE TO RELATED APPLICATIONS

This is a Continuation Application of PCT Application No. PCT/JP2017/044940, filed Dec. 14, 2017, the entire contents of which are incorporated herein by reference.

BACKGROUND

A treatment target, such as biological tissue, can be treated by using an ultrasonic treatment device that generates and transmits ultrasonic vibration.

The vibration transmitter is formed of two separable members. The vibration transmitter is formed by joining two separately formed members. The two members are joined by screw fastening. At the screw fastened joint, the positional relationship between the two joined members is defined by the machining accuracy of when the two members are manufactured. Therefore, since the positional relationship between the two members is difficult to be adjusted after they are joined, it is difficult to adjust the positional relationship when joining the two members.

SUMMARY

The present disclosure relates generally to a vibration transmitter that transmits ultrasonic vibration, and an ultrasonic treatment device for treating a treatment target using ultrasonic vibration.

According to an exemplary embodiment, a vibration transmitter includes: a first rod including a fitting hole extending along the longitudinal axis; and a second rod attached to a distal end portion of the first rod by a fitting portion into the fitting hole in a state where a compressed surface pressure is received from the fitting hole. The first rod includes: a first region in which the fitting portion is fitted into the fitting hole; and a second region positioned proximal of the first region. In the first region of the first rod, a crystal grain diameter is larger than that in the second region of the first rod.

According to an exemplary embodiment, an ultrasonic treatment device includes: a transducer configured to generate ultrasonic vibration; a housing in which the transducer is provided; and a vibration transmitter including first and second rods. The vibration transmitter is capable of transmitting vibration of a predetermined resonance frequency generated by the transducer from a proximal part of the first rod to a distal end of the second rod along the longitudinal axis. In a state where the vibration transmitter vibrates at the predetermined resonance frequency, an antinode of vibration closest to a proximal end of the second rod is positioned distal of the proximal end of the second rod.

DETAILED DESCRIPTION

An exemplary embodiment of the present disclosure will be explained with reference to FIG. 1 to FIG. 4.

Figure 1:
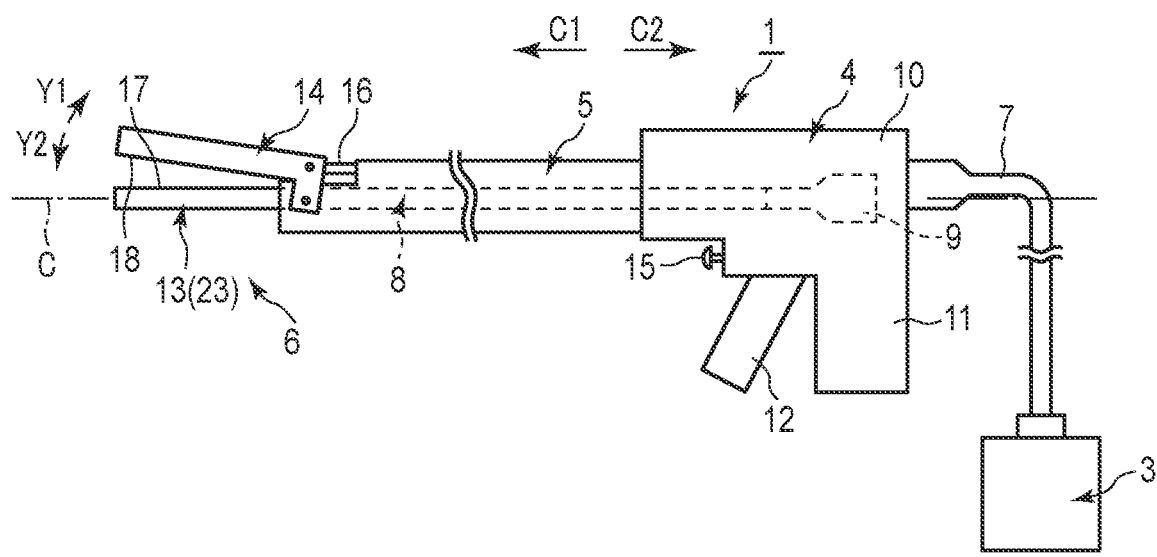
FIG. 1 is a schematic view showing an ultrasonic treatment device according to an exemplary embodiment.

FIG. 1 shows a treatment device 1, which is an ultrasonic treatment device of the present embodiment. As shown in FIG. 1, the treatment device 1 includes a housing 4 and a cylindrical shaft 5 coupled to the housing 4. The housing 4 can be held by hand. One end of a cable 7 is connected to the housing 4. The other end of the cable 7 is detachably connected to a power source device 3.

The shaft 5 defines a longitudinal axis C. Here, a direction along the longitudinal axis C will be referred to as a longitudinal direction. One side of the longitudinal direction will be referred to as a distal side (an arrow C1 side in FIG. 1), and a side opposite to the distal side will be referred to as a proximal side (an arrow C2 side in FIG. 1). The shaft 5 is coupled to the distal side of the housing 4 and extends along the longitudinal axis C from the proximal side to the distal side.

An end effector 6 is provided on a distal part of the shaft 5. The end effector 6 includes a first grasping piece 13 and a second grasping piece 14. The first grasping piece 13 and the second grasping piece 14 can be opened and closed. The first grasping piece 13 is supported by the shaft 5, and the second grasping piece 14 is rotatably attached to the shaft 5 with respect to the first grasping piece 13.

The first grasping piece 13 is provided with a treatment surface (opposed surface) 17 which faces the second grasping piece 14 and applies treatment energy to a treatment target. The second grasping piece 14 is provided with a treatment surface (opposed surface) 18 which faces the treatment surface 17 of the first grasping piece 13 and applies treatment energy to the treatment target.

The opening and closing directions of the end effector 6 intersect with (are perpendicular or substantially perpendicular to) the longitudinal axis C. Of the opening and closing directions of the end effector 6, a side on which the second grasping piece 14 opens relative to the first grasping piece 13 will be referred to as an opening direction of the second grasping piece 14 (arrow Y1), and a side on which the second grasping piece 14 closes relative to the first grasping piece 13 will be referred to as a closing direction of the second grasping piece 14 (arrow Y2). Also, a direction intersecting with (perpendicular or substantially perpendicular to) the longitudinal axis C and intersecting with (perpendicular or substantially perpendicular to) the opening and closing directions of the end effector 6 will be referred to as a width direction of the end effector 6.

As shown in FIG. 1, the housing 4 includes a housing main body 10 and a grip (fixed handle) 11. The housing main body 10 extends along the longitudinal axis C. The grip 11 extends from the housing main body 10 toward a side away from the longitudinal axis C. The shaft 5 is coupled to the housing main body 10 from the distal side.

A movable handle 12 is rotatably attached to the housing main body 10. The movable handle 12 is positioned near the grip 11 with respect to the longitudinal axis C, and, in the present embodiment, is positioned on the distal side with respect to the grip 11. When the movable handle 12 rotates relative to the housing main body 10, the movable handle 12 opens or closes with respect to the grip 11. When the movable handle 12 opens or closes with respect to the grip 11, an operation to open or close the end effector 6 in the manner described above is input at the movable handle 12. That is, the movable handle 12 is an open/close operation input unit.

The movable handle 12 and the second grasping piece 14 are coupled to each other via a movable member 16. The movable member 16 extends along the longitudinal axis C inside the shaft 5. When the movable handle 12 opens or closes with respect to the grip 11, the movable member 16 moves along the longitudinal axis C relative to the shaft 5 and the housing 4, and the second grasping piece 14 rotates relative to the shaft 5. This allows the grasping pieces 13 and 14 to open or close. When the grasping pieces 13 and 14 are closed toward each other in a state where a treatment target is disposed between the grasping pieces 13 and 14, the treatment target is thereby grasped between the grasping pieces 13 and 14.

The power source device 3, as an example, includes a high-frequency power source and an ultrasonic power source. In the present embodiment, an example of the power source device 3 including both a high-frequency power source and an ultrasonic power source is explained; however, the power source device 3 according to the present embodiment need only include an ultrasonic power source. The high-frequency power source includes a waveform generator, a conversion circuit, and a transformer, etc., and converts power from a battery power source or an outlet power source, etc. into high-frequency power. Furthermore, at least a part of each of the first grasping piece 13 and the second grasping piece 14 is made of an electrically conductive material such as metal. The high-frequency power source is electrically connected to the electrically conductive material of each of the first grasping piece 13 and the second grasping piece 14 via an electric path provided through the inside of the cable 7, the inside of the housing 4, and the inside of the shaft 5. The high-frequency power source outputs the converted high-frequency power through the above-described electric path, and supplies the high-frequency power to the first grasping piece 13 and the second grasping piece 14 as electric energy. When the high-frequency power is supplied to the first grasping piece 13 and the second grasping piece 14 in a state where the treatment target is grasped between the first grasping piece 13 and the second grasping piece 14, a high-frequency electric current flows between the first grasping piece 13 and the second grasping piece 14 via the treatment target. As a result, the high-frequency electric current is applied to the treatment target as the treatment energy.

The ultrasonic power source includes a waveform generator, a conversion circuit, and a transformer, etc., and converts the power from the battery power source or the outlet power source, etc. into AC power. Furthermore, an ultrasonic transducer 9 and a vibration transmitter (ultrasonic probe) 8 that is detachably connected to the distal side of the ultrasonic transducer 9 are provided inside the housing main body 10. The ultrasonic power source is electrically connected to the ultrasonic transducer 9 via an electric path provided through the inside of the cable 7 and the inside of the housing 4. When the electric energy (AC power) is supplied from the ultrasonic power source to the ultrasonic transducer 9, ultrasonic vibration is generated at the ultrasonic transducer 9. The ultrasonic vibration generated at the ultrasonic transducer 9 is transmitted to the vibration transmitter 8. In the present embodiment, the ultrasonic vibration generated at the ultrasonic transducer 9 is longitudinal vibration that is displaced along the longitudinal direction, and is transmitted along the longitudinal direction from the proximal end toward the distal end of the vibration transmitter 8.

The vibration transmitter 8 is preferably made of a material that has high vibration transmissibility and is suitable for transmitting ultrasonic vibration. The vibration transmitter 8 is made of, for example, a titanium alloy, an aluminum alloy, stainless steel, ceramic, and metallic glass. The ultrasonic transducer 9 and the vibration transmitter 8 form one vibrating body (ultrasonic treatment device). When the ultrasonic vibration generated at the ultrasonic transducer 9 is transmitted to the distal end of the vibration transmitter 8, the vibrating body including the ultrasonic transducer 9 and the vibration transmitter 8 vibrates integrally.

The vibration transmitter 8 extends from the inside of the housing main body 10 to the distal side thereof, passes through the inside of the shaft 5, and protrudes from the distal end of the shaft 5 to the distal side thereof. A projecting portion of the vibration transmitter 8 from the shaft 5 toward the distal side thereof constitutes the first grasping piece 13. The ultrasonic vibration generated at the ultrasonic transducer 9 is transmitted to the distal part of the vibration transmitter 8 forming the first grasping piece 13. As a result, the ultrasonic vibration is transmitted to the first grasping piece 13 as the treatment energy. When the ultrasonic vibration is transmitted to the first grasping piece 13 in a state where the treatment target is grasped between the first grasping piece 13 and the second grasping piece 14, the ultrasonic vibration is applied to the treatment target as the treatment energy.

The housing main body 10 is provided with an operation button 15. The operation button 15 is an energy operation input unit. When the operation is input by the operation button 15 in a state where the treatment target is grasped between the grasping pieces 13 and 14, for example, the electric energy is supplied to the treatment device 1 from each of the high-frequency power source and the ultrasonic power source. The high-frequency electric current and the ultrasonic vibration are applied to the grasped treatment target as the treatment energy. In one embodiment, a foot switch electrically connected to the power source device 3 is provided separately from the treatment device 1, instead of or in addition to the operation button 15.

In one embodiment, a plurality of operation buttons 15 are provided on the housing main body 10. When an operation is input by a certain button among the plurality of operation buttons 15 in a state where the treatment target is grasped, for example, only the high-frequency electric current is applied to the treatment target as the treatment energy. Furthermore, when an operation is input by another certain button among the plurality of operation buttons 15 in a state where the treatment target is grasped, for example, the high-frequency electric current and the ultrasonic vibration are applied to the treatment target as the treatment energy.

Furthermore, in another embodiment, an operation member such as a rotary knob is attached to the housing main body 10. In this case, when the operation member is rotated about the longitudinal axis C with respect to the housing 4, the shaft 5 and the end effector 6 rotate about the longitudinal axis C with respect to the housing 4 together with the operation member.

Figure 2:
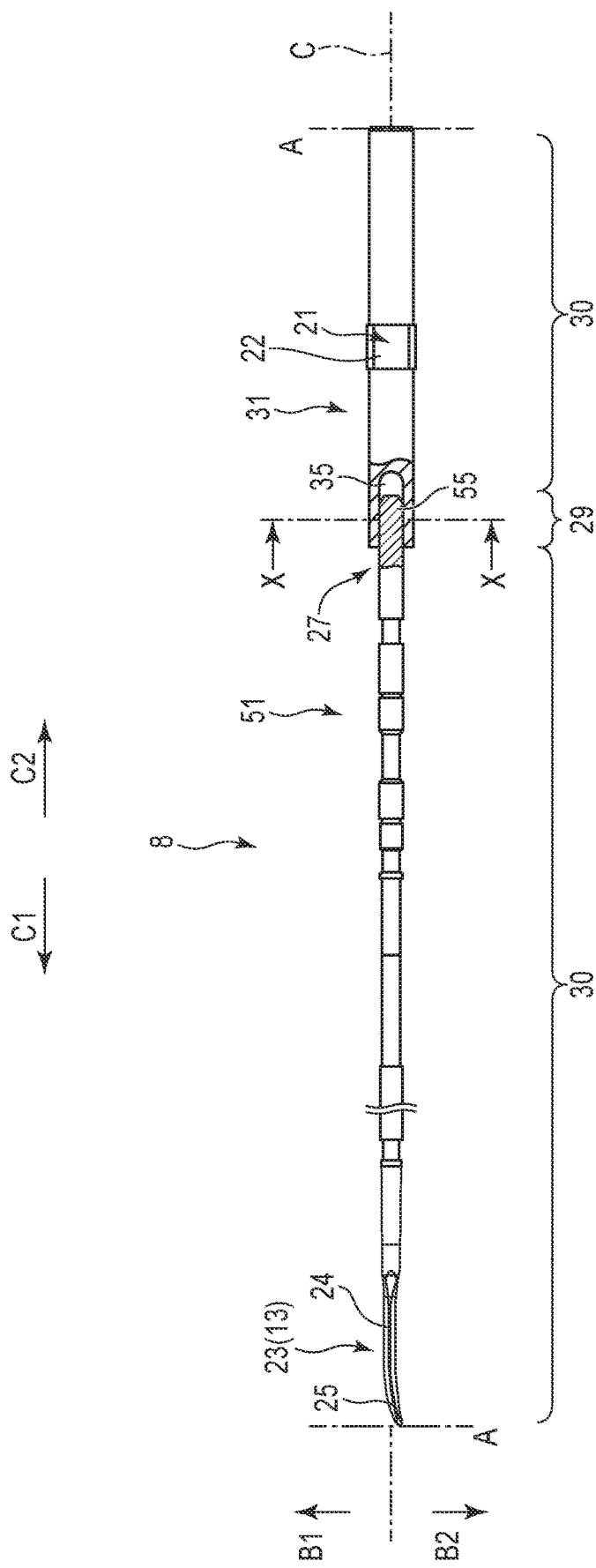
FIG. 2 is a schematic view showing a partial cross section of a vibration transmitter according to the exemplary embodiment.

FIG. 2 is a diagram showing the vibration transmitter 8. The shape including a length, a diameter, and a cross-sectional shape and the material of the vibration transmitter 8 are set as appropriate so as to vibrate at a predetermined resonance frequency f. The predetermined resonance frequency f is, for example, any frequency between 20 kHz and 60 kHz, and, in one embodiment, it is any frequency between 43 kHz and 50 kHz. The total length of the vibrating body including the ultrasonic transducer 9 and the vibration transmitter 8 is an integral multiple of a half-wavelength ($\lambda/2$) of the ultrasonic vibration to be transmitted. The half-wavelength ($\lambda/2$) of the ultrasonic vibration is determined by the resonance frequency f of the vibrating body including the ultrasonic transducer 9 and the vibration transmitter 8, and the physical properties of the material of the vibrating body including the ultrasonic transducer 9 and the vibration transmitter 8, etc.

In a state where the vibrating body including the ultrasonic transducer 9 and the vibration transmitter 8 vibrates at a predetermined resonance frequency f, an antinode of vibration and a node of vibration are positioned alternately along the longitudinal axis C in the vibration transmitter 8. The distal end of the vibration transmitter 8 and the proximal end of the vibration transmitter 8 become antinode positions A. Furthermore, inside the shaft 5, the vibration transmitter 8 is supported by the shaft 5 on the outer circumference of a position to be a node position via, for example, a rubber material.

The distance between adjacent vibrating nodes is a half-wavelength of the vibration, that is, $\lambda/2$. Similarly, the distance between adjacent vibrating antinodes is a half-wavelength of the vibration, that is, $\lambda/2$. Furthermore, the distance between the adjacent antinode of vibration and node of vibration is a quarter wavelength of the vibration, that is, $\lambda/4$. The $\lambda/4$ varies depending on the resonance frequency f of the vibrating body. In a case where the resonance frequency f is 43 kHz to 50 kHz, the $\lambda/4$ is 20 mm to 30 mm.

The vibration transmitter 8 includes a first rod member 31 and a second rod member 51. The second rod member 51 is positioned on the distal side of the longitudinal direction relative to the first rod member 31. The first rod member 31 and the second rod member 51 are separate members. The distal part of the first rod member 31 and the proximal part of the second rod member 51 are joined. The first rod member 31 and the second rod member 51 are joined by, for example, shrinkage fitting, press-fitting, caulking, and forging. In one embodiment, in addition to these joining methods, reinforcement by adhesives or the like may be performed. The first rod member 31 is formed thicker than the second rod member 51. That is, the diameter of the first rod member 31 is larger than the diameter of the second rod member 51. The area of inner cross section of the outermost edge of the first rod member 31 is larger than the area of inner cross section of the outermost edge of the second rod member 51.

The first rod member 31 is extended along the longitudinal axis C. The proximal end of the first rod member 31 forms the proximal end of the vibration transmitter 8. The first rod member 31 is preferably made of a material that has high vibration transmissibility and is suitable for transmitting ultrasonic vibration. The first rod member 31 is made of, for example, an aluminum alloy. As the aluminum alloy, an Al—Cu alloy, an Al—Mg alloy, ultra duralumin, super duralumin, and the like are used.

The first rod member 31 includes a flange 21. The flange 21 is a part formed to have the thickest diameter in the vibration transmitter 8. The flange 21 is provided on the outer circumference of a position to be the position of the node of vibration when vibrating the vibrating body. Therefore vibration displacement in the longitudinal direction is unlikely to occur at the flange 21. The vibration transmitter 8 is supported at the flange 21, inside the housing main body 10. The flange 21 includes a planar part 22 whose cross section intersecting with (perpendicular to or substantially perpendicular to) the longitudinal axis C is formed substantially polygonal, and which extends substantially parallel to the longitudinal axis C.

The second rod member 51 is extended along the longitudinal axis C. The distal end of the second rod member 51 forms the distal end of the vibration transmitter 8. The second rod member 51 is preferably made of a material that has high vibration transmissibility and is suitable for transmitting ultrasonic vibration. The second rod member 51 is made of, for example, a titanium alloy. Titanium alloy is higher in strength than aluminum alloy. That is, the second rod member 51 is formed of a material with higher strength than the material forming the first rod member 31.

The second rod member 51 includes a distal end treatment portion 23 that forms the first grasping piece 13. The distal end treatment portion 23 forms a distal part of the second rod member 51. The shape of the distal end treatment portion 23 is determined by a treatment performed using the treatment device 1, and is formed into a shape suitable for the treatment to be performed. In the present embodiment, the distal end treatment portion 23 includes a straight portion 24 extending along the longitudinal axis C and a curved portion 25 provided on the distal side of the straight portion 24. The curved portion 25 is curved toward one side of the width direction (an arrow B1 side and an arrow B2 side of FIG. 2) of the end effector 6 with respect to the straight portion 24 and the longitudinal axis C. The curved portion 25 has at least one curved surface tilted with respect to the longitudinal axis C. The curved portion 25 is formed by a combination of one or more curved surfaces and one or more planar surfaces.

The second rod member 51 includes at least one maximum outer diameter portion 27. The maximum outer diameter portion 27 is the thickest portion of the second rod member 51, that is, a portion with the largest outer diameter. Therefore, the maximum outer diameter portion 27 is a maximum cross-section area portion at which an area (cross-section area) of the cross section orthogonal (substantially perpendicular) to the longitudinal axis C becomes the largest in the second rod member 51. The maximum outer diameter portion 27 is not formed as a portion that is directly held by the housing main body 10, which is different from the flange 21 of the first rod member 31. The maximum outer diameter portion 27 is used to adjust the vibration velocity and the denaturation ratio of the ultrasonic vibration in the second rod member 51. In the present embodiment, the maximum outer diameter portion 27 is provided at the proximal part of the second rod member 51 and extends from a proximal surface 53 of the second rod member 51 to the distal side thereof.

Figure 3:
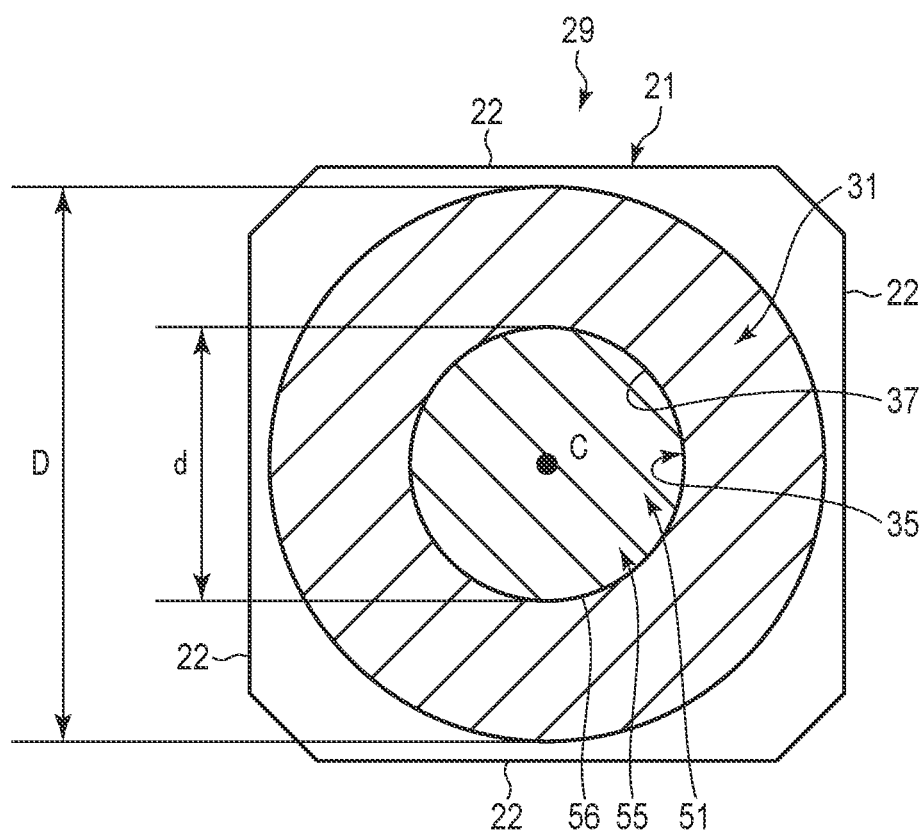
FIG. 3 is a cross-sectional view taken along a line X-X of FIG. 2.
Figure 4:
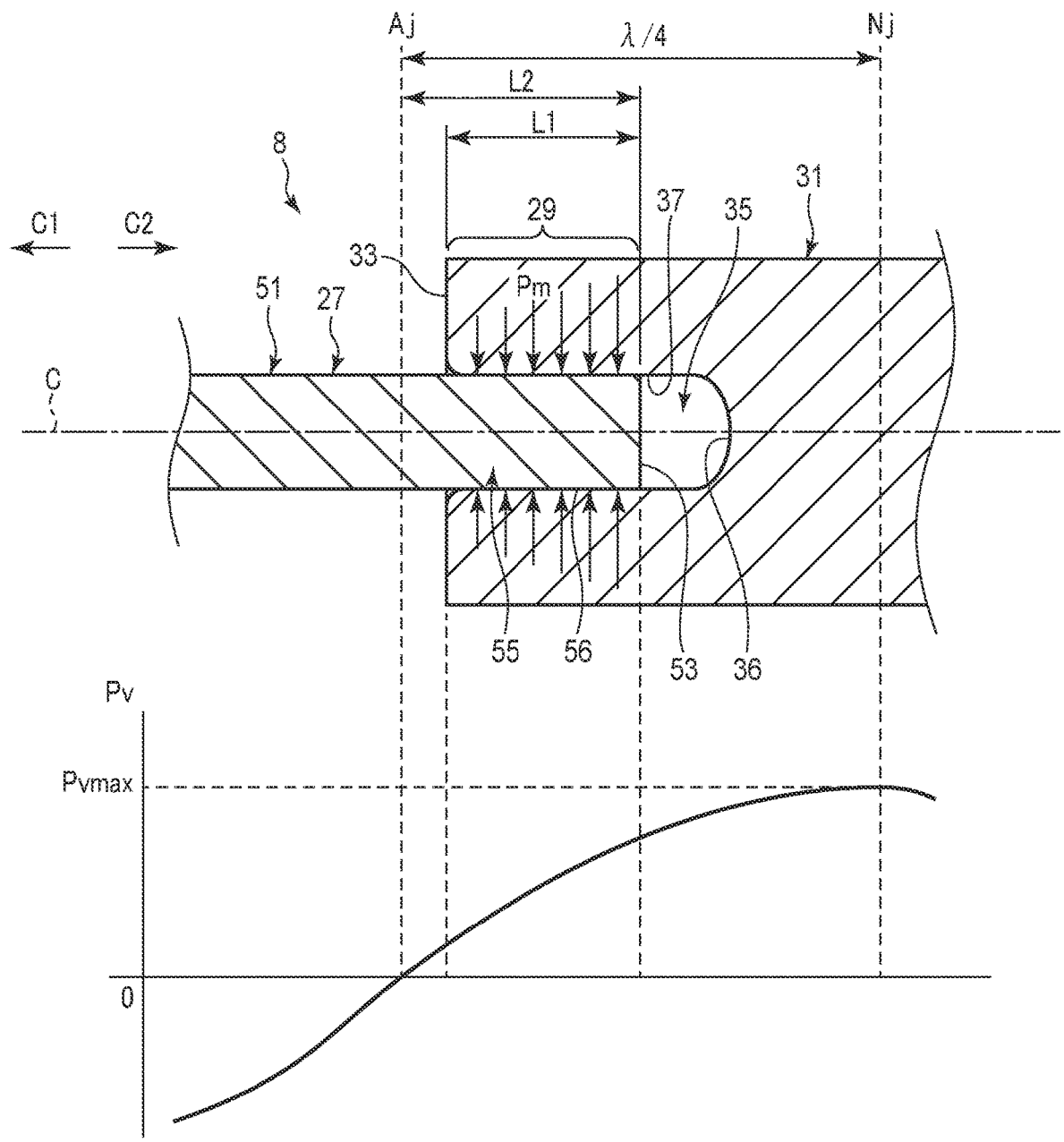
FIG. 4 is a schematic view showing a configuration of a joint between a first rod member and a second rod member, and distribution of stress caused by vibration in a longitudinal direction in a cross section taken along a longitudinal axis in the vibration transmitter according to an exemplary embodiment.

FIG. 3 is a cross-sectional view taken along a line X-X of FIG. 2. FIG. 3 shows a cross section intersecting with (substantially perpendicular to) the longitudinal axis C. FIG. 4 shows a configuration of a joint between the first rod member 31 and the second rod member 51. FIG. 4 shows a cross section passing through the longitudinal axis C.

As shown in FIG. 3 and FIG. 4, the first rod member 31 includes a fitting hole 35. The fitting hole 35 is a groove extending along the longitudinal axis C from a distal surface 33 of the first rod member 31 toward the proximal side thereof. The fitting hole 35 is provided with a bottom surface 36 that intersects with the longitudinal axis C and an inner circumferential surface 37 that extends about the longitudinal axis C. In the present embodiment, the cross-sectional shape of the fitting hole 35 intersecting with (perpendicular or substantially perpendicular to) the longitudinal axis C is substantially round.

The second rod member 51 includes a fitting portion 55. The fitting portion 55 is provided at the proximal part of the second rod member 51, and is fitted into the fitting hole 35 of the first rod member 31. The outer diameter of the fitting portion 55 is substantially equal to the inner diameter d of the fitting hole 35 in a state where it is fitted into the fitting hole 35. The fitting portion 55 is formed in the longitudinal direction in a range from the distal surface 33 of the first rod member 31 to the proximal surface 53 of the second rod member 51. In the present embodiment, the cross-sectional shape of the fitting portion 55 intersecting with (perpendicular or substantially perpendicular to) the longitudinal axis C is substantially round. In the present embodiment, the fitting portion 55 is formed by a portion of the maximum outer diameter portion 27. That is, a part of the maximum outer diameter portion 27 forms the fitting portion 55.

Here, as shown in FIG. 2, in the vibration transmitter 8, a region in which the fitting portion 55 of the second rod member 51 is fitted into the fitting hole 35 of the first rod member 31 will be referred to as a fitting region (a first region) 29, and a portion other than the fitting region 29 will be referred to as a non-fitting region (a second region) 30. A length (fitting length) L1 of the fitting region (joint region) 29 in the longitudinal direction corresponds to a distance between the distal surface 33 of the first rod member 31 and the proximal surface 53 of the second rod member 51. The length (fitting length) L1 of the fitting region 29 is, for example, 2 mm to 10 mm.

In the fitting region 29, the inner circumferential surface 37 of the fitting hole 35 of the first rod member 31 is closely attached to the outer circumferential surface 56 of the fitting portion 55 of the second rod member 51 from the outside. Furthermore, the length L1 of the fitting portion 55 in the longitudinal direction is shorter than the length of the fitting hole 35 in the longitudinal direction. Therefore, a gap is formed between the proximal surface 53 of the second rod member 51 and the bottom surface 36 of the fitting hole 35. That is, the proximal surface 53 of the fitting portion 55 of the second rod member 51 and the bottom surface 36 of the fitting hole 35 of the first rod member 31 do not come in contact with each other.

As described above, in the fitting region 29, the outer circumferential surface 56 of the fitting portion 55 of the second rod member 51 and the inner circumferential surface 37 of the fitting hole 35 of the first rod member 31 come in contact with each other, and the proximal surface 53 of the fitting portion 55 and the bottom surface 36 of the fitting hole 35 do not come in contact with each other. Therefore, the first rod member 31 and the second rod member 51 come in contact with each other only at a portion where they extend substantially parallel to the longitudinal axis C in the fitting region 29.

An outer diameter D of the first rod member 31 in the fitting region 29 is preferably smaller than the inner diameter of a trocar used for the surgical procedure using the treatment device 1. The inner diameter of the trocar is, for example, 10 mm. Moreover, preferably, the outer diameter D of the first rod member 31 in the fitting region 29 is formed equal to or smaller than ¼ of the wavelength λ of the vibration, that is, equal to or smaller than λ/4.

Here, an example of a manufacturing method of the vibration transmitter 8 will be explained briefly. When manufacturing the vibration transmitter 8, an operator first forms the first rod member 31 and the second rod member 51, respectively, by cutting, etc.

Then, the operator joins the first rod member 31 and the second rod member 51. The first rod member 31 and the second rod member 51 are joined by shrinkage fitting, press-fitting, and the like. Here, as an example of a method of joining the first rod member 31 and the second rod member 51, the joining performed by shrinkage fitting will be briefly explained.

When the joining is performed by the shrinkage fitting, the operator first fixes the first rod member 31 in a joining apparatus, and heats the fitting region 29 of the first rod member 31. The first rod member 31 thermally expands when heated. As a result, the inner diameter of the fitting hole 35 is enlarged, and the inner circumferential surface 37 of the fitting hole 35 moves outward. The first rod member 31 is heated until the inner diameter of the fitting hole 35 becomes larger than the outer diameter of the fitting portion 55 of the second rod member 51.

Then, the second rod member 51 fixed in the joining apparatus is moved to insert the fitting portion 55 into the fitting hole 35 from the distal side thereof. At this time, since the fitting hole 35 is enlarged in the manner described above, the fitting portion 55 can be easily inserted into the fitting hole 35.

The positional relationship between the first rod member 31 and the second rod member 51 is then adjusted. In one embodiment, a reference index (a first index) defining a reference position is provided for the first rod member 31, and an index (a second index) indicating a positional relationship with the reference index is provided for the second rod member 51. Then, by correlating the first index of the first rod member 31 with the second index of the second rod member 51, the positional relationship between the first rod member 31 and the second rod member 51 is adjusted in the longitudinal direction and in a rotation direction about the longitudinal axis C.

In one embodiment, the fitting hole 35 of the first rod member 31 is formed in a D-cut shape and is provided with a planar surface extending along the longitudinal direction. The fitting portion 55 of the second rod member 51 is also formed in a D-cut shape corresponding to the D-cut shape of the fitting hole 35. In this case, by fitting the fitting portion 55 into the fitting hole 35, the positional relationship between the first rod member 31 and the second rod member 51 is adjusted about the longitudinal axis C (rotation direction). In this case, a planar part (first reference surface) formed on the inner circumferential surface 37 of the fitting hole 35 by the D-cut shape becomes the first index, and a planar part (second reference surface) formed on the outer circumferential surface 56 of the fitting portion 55 by the D-cut shape becomes the second index.

In one embodiment, one of the planer parts 22 of the flange 21 is used as the first index (first reference surface), and one of the curved surface or the planer surface of the curved portion 25 of the second rod member 51 is used as the second index (second reference surface).

Then, the operator cools the first rod member 31 in a state where the positional relationship between the first rod member 31 and the second rod member 51 is adjusted. The first rod member 31 is contracted by being cooled from the heated state. When the first rod member 31 is contracted, the inner circumferential surface 37 of the fitting hole 35 shrinks. As a result, the inner circumferential surface 37 of the fitting hole 35 is attached closely to the outer circumferential surface 56 of the fitting portion 55 of the second rod member 51 from outside. The outer circumferential surface 56 of the fitting portion 55 is pressed inwardly by the inner circumferential surface 37 of the fitting hole 35, and compressed surface pressure (joining stress) Pm acts on the outer circumferential surface 56 of the fitting portion 55.

As described above, in the joining method performed by shrinkage fitting, heat treatment is performed on the first rod member 31 in the fitting region 29. At a portion on which the heat treatment is performed, crystals in a material are recrystallized, thereby coarsening the material and increasing the crystal grain diameter. Furthermore, the strength of the portion on which the heat treatment is performed decreases. Therefore, in the first rod member 31, the strength becomes lower, and the crystal grain diameter becomes larger in comparison to the portion on which the heat treatment is not performed in the fitting region 29 and in the vicinity of the fitting region 29.

In one embodiment, after the step of adjusting the positional relationship between the first rod member 31 and the second rod member 51, a step of reheating the first rod member 31 is performed before the step of cooling the first rod member 31. In this case, the first rod member 31 and the second rod member 51 are both heated by heat in the fitting region 29 and the vicinity of the fitting region 29. Therefore, the strength decreases, and the crystal grain diameter in the material increases also for the second rod member 51 in the fitting region 29 (fitting portion 55) and the vicinity of the fitting region 29. Therefore, also in the second rod member 51, the strength becomes lower, and the crystal grain diameter becomes larger in comparison to the other portions in the fitting region 29 (fitting portion 55) and in the vicinity of the fitting region 29.

The fitting hole 35 of the first rod member 31 is formed to have a substantially constant inner diameter. Furthermore, in the fitting hole 35, the distal end is opened. Therefore, rigidity and strength, etc. decrease near the opening of the fitting hole 35. When the rigidity and strength, etc. near the opening of the fitting hole 35 decrease, compressed surface pressure Pm that presses the fitting portion 55 decreases. Thus, the compressed surface pressure Pm decreases from the bottom surface 36 toward the opening side, that is, from the proximal side toward the distal side. In this manner, the magnitude of the compressed surface pressure Pm varies in the longitudinal direction.

In the case of ignoring the change in the compressed surface pressure Pm in the longitudinal direction, the magnitude of the compressed surface pressure Pm (MPa) acting on the outer circumferential surface 56 of the fitting portion 55 can be approximated by using formula (1).

$$Pm = \frac{\Delta d}{d} \times \frac{1}{\left[\frac{m_s - 1}{m_s E_s} - \frac{m_i - 1}{m_i E_i}\right] + \frac{2}{E_i(1 - k^2)}} \quad \text{[Formula 1]}$$

Here, "mi" represents the Poisson number of the first rod member 31, and "ms" represents the Poisson number of the second rod member 51. Furthermore, "Ei (MPa)" represents a longitudinal elastic modulus of the first rod member 31, and "Es (MPa)" represents a longitudinal elastic modulus of the second rod member 51. The inner diameter of the fitting hole 35 and the outer diameter of the fitting portion 55 are expressed by "d (mm)", the outer diameter of the first rod member 31 in the fitting region 29 is expressed by "D (mm)", and a "k" is a coefficient expressed by d/D. "Δ d (mm)" represents interference, which is a dimensional difference between the inner diameter of the fitting hole 35 before joining and the outer diameter of the fitting portion 55 before joining.

Note that formula (1) is a computation expression in the case where the second rod member 51 is solid. The magnitude of the compressed surface pressure Pm (MPa) in the case where the second rod member 51 is hollow can be approximated by using formula (2).

$$Pm = \frac{\Delta d}{d} \times \frac{1}{\left[\frac{m_s - 1}{m_s E_s} - \frac{m_i - 1}{m_i E_i}\right] + 2\left[\frac{k_0^2}{E_s(1 - k_0^2)} + \frac{1}{E_i(1 - k^2)}\right]} \quad \text{[Formula 2]}$$

Here, "k0" is a coefficient expressed by "d0/d" using an inner diameter "d0 (mm)" of a hollow portion of the second rod member 51.

The vibration transmitter 8 is formed in a manner of satisfying V/Pm≤Rth in the fitting region 29. Here, "V (m/s)" represents the vibration velocity of the vibration transmitter 8 in the fitting region 29. The threshold value "Rth ((m/s)/MPa)" is a boundary value (oscillation limit value) that allows the first rod member 31 and the second rod member 51 to be joined in a resonated (oscillated) manner. In the present embodiment, the threshold value Rth is 0.176. The threshold value Rth is adjusted by adjusting, for example, the compressed surface pressure Pm. The compressed surface pressure Pm may also be adjusted by, for example, adjusting interference Δd.

Joining strength (joining torque) S of the first rod member 31 and the second rod member 51 is approximated by using a formula "S=F·μ·(d/2)". Here, "μ" is a friction coefficient between the outer circumferential surface 56 of the fitting portion 55 and the inner circumferential surface 37 of the fitting hole 35. "F (N)" represents a load applied to the outer circumferential surface 56 of the fitting portion 55. The load F is calculated by a formula "F=Pm·π·d·L1". Therefore, a joining strength S is calculated by a formula "S=Pm·π·d·L1·μ·d/2".

The vibration transmitter 8 is formed in a manner that the joining strength S becomes higher than a threshold value Sth in the fitting region 29. The joining strength S is adjusted to a magnitude that is equal to or higher than the threshold value Sth by, for example, adjusting the length L1 of the fitting portion 55. The threshold value Sth is, for example, a maximum value of a torque that may be applied to the treatment device 1 during surgery using the treatment device 1. The threshold value Sth is, for example, 0.020 (N·m). In this case, the length (fitting length) L1 of the fitting region 29 satisfies the relational expression of the following formula (3).

$$64/(Pm \times d^2) \leq L1 \quad \text{[Formula 3]}$$

In the present embodiment, an antinode position Aj of the vibration is positioned at a position slightly deviated to the distal side than the distal surface 33 of the first rod member 31. That is, the antinode position Aj of the vibration is positioned at a position slightly deviated to the distal side than the fitting region 29. The antinode position Aj is an antinode of the vibration closest to the distal surface 33 of the first rod member 31 and the fitting region 29. A node position Nj adjacent to the proximal side with respect to the antinode position Aj becomes a node of the vibration closest to the distal surface 33 of the first rod member 31 and the fitting region 29.

In the vibration transmitter 8, the displacement caused by the ultrasonic vibration is 0 at the node position (for example, Nj) of the vibration, and increases toward the antinode (for example, Aj) of vibration. The displacement caused by the ultrasonic vibration becomes the largest at the antinode (for example, Aj) of vibration. However, the magnitude of displacement at each position in the longitudinal direction varies according to the shape and material of the vibration transmitter 8, and is therefore, not limited to the above.

A waveform chart of FIG. 4 shows a change of stress (vibration stress) Pv in the longitudinal direction acting on the vibration transmitter 8 caused by the ultrasonic vibration. A horizontal axis in the waveform chart of FIG. 4 shows positions in the longitudinal direction. A vertical axis in the waveform chart of FIG. 4 shows the stress Pv acting on the vibration transmitter 8. In the present embodiment, since the ultrasonic vibration is longitudinal vibration, the stress Pv is a force directed to one side of the longitudinal direction. Here, the force acting on one side of the longitudinal direction (for example, tensile stress) is referred to as a positive stress Pv, and the force acting on the other side (for example, compressive stress) is referred to as a negative stress. The magnitude of the stress Pv is expressed by an absolute value of the stress Pv.

As shown in FIG. 4, the magnitude of the stress Pv acting on the vibration transmitter 8 caused by the ultrasonic vibration is 0 at the antinode of vibration (for example, Aj), and becomes larger toward the node of vibration (for example, Nj). The magnitude of the stress Pv reaches maximum (Pv=Pvmax) at the node of the vibration (for example, Nj). However, the magnitude of the stress Pv at each position in the longitudinal direction varies according to the shape and material of the vibration transmitter 8, therefore, is not limited to the above.

The proximal surface 53 of the fitting portion 55 of the second rod member 51 is positioned on the proximal side of the antinode position Aj, and on the distal side of the node position Nj. That is, the proximal surface 53 is positioned between the antinode position Aj and the node position Nj in the longitudinal direction. A distance L2 between the antinode position Aj and the proximal surface 53 is shorter than λ/4. The antinode position Aj is an antinode position closest to the proximal surface 53, and the node position Nj is a node position closest to the proximal surface 53.

As described above, the antinode position Aj is an antinode position closest to the fitting region 29, and the node position Nj is a node position closest to the fitting region 29. Therefore, the antinode position Aj closest to the proximal surface 53 and the fitting region 29 is positioned on the distal side of the proximal surface 53.

Furthermore, the bottom surface 36 of the fitting hole 35 of the first rod member 31 is positioned on the proximal side of the antinode position Aj, and on the distal side of the node position Nj. That is, the bottom surface 36 is positioned between the antinode position Aj and the node position Nj in the longitudinal direction. Therefore, the distance between the antinode position Aj closest to the proximal surface 53 of the second rod member 51 and the bottom surface 36 is smaller than λ/4. Furthermore, the distal surface 33 of the first rod member 31 is positioned on the proximal side of the antinode position Aj, and on the distal side of the node position Nj. That is, the distal surface 33 of the first rod member 31 is positioned between the antinode position Aj and the node position Nj in the longitudinal direction. Therefore, the length L1 of the fitting portion 55 in the longitudinal direction becomes smaller than λ/4.

As described above, in the present embodiment, the fitting portion 55 is formed by a part of the maximum outer diameter portion 27. Therefore, the maximum outer diameter portion 27 is positioned at least in part within the range of the fitting region 29.

Operations and effects of the treatment device 1 of the present embodiment will now be explained. When performing treatment using the treatment device 1, first, the end effector 6 is inserted into a body cavity, such as an abdominal cavity. Then, a treatment target, such as a blood vessel, is disposed between a pair of grasping pieces 13 and 14, and the end effector 6 is closed. Thus, the treatment target is grasped between the grasping pieces 13 and 14. When an operation to supply electric energy from the power source device 3 to the treatment device 1 is input in a state where the treatment target is grasped between the grasping pieces 13 and 14, at least one of the high-frequency current or the ultrasonic vibration is applied to the grasped treatment target as the treatment energy.

In the present embodiment, the vibration transmitter 8 includes the first rod member 31 including the flange 21 and the second rod member 51 including the distal end treatment portion 23, and is manufactured by joining the two members of the first rod member 31 and the second rod member 51. Therefore, when manufacturing the vibration transmitter 8, it is possible to form the first rod member 31 having a large outer diameter and the second rod member 51 having a small outer diameter separately. Here, when manufacturing each of the first rod member 31 and the second rod member 51, the cutting amount can be reduced by cutting a material with a diameter the same size as or slightly larger than the outer diameter of each of the first rod member 31 and the second rod member 51. Furthermore, as the flange 21 supported in the housing main body 10 is formed on the first rod member 31, it does not need to be formed on the second rod member 51. Therefore, compared to a case in which the flange is formed on the second rod member 51, a difference in the cross-sectional area (difference in outer diameter) can be made smaller between regions in which areas of a cross section substantially perpendicular to the longitudinal axis C are maximized and minimized in the second rod member 51. As a result, in particular, the cutting amount of when the second rod member 51 is manufactured can be reduced, and the manufacturing cost of the vibration transmitter 8 can be reduced.

Here, unlike the present embodiment, in a configuration where a first rod member and a second rod member are joined by screw fastening, in the case of adjusting the positional relationship between the first rod member and the second rod member in the longitudinal direction, for example, the second rod member must be rotated about the longitudinal axis C relative to the first rod member. Furthermore, in the case of adjusting the positional relationship between the first rod member and the second rod member about the longitudinal axis C (rotation direction), the second rod member rotates about the longitudinal axis C relative to the first rod member, and moves relative to the first rod member in the longitudinal direction. Therefore, in the joining method achieved by screw fastening, it is difficult to adjust the first rod member and the second rod member in terms of the positional relationship in the longitudinal direction and the rotation (rotation direction) about the longitudinal axis C, separately.

On the other hand, in the present embodiment, the first rod member 31 and the second rod member 51 are joined by press-fitting and shrinkage fitting, etc., and are joined under the compressed surface pressure Pm. In the joining method achieved by press-fitting and shrinkage fitting, etc., when joining the first rod member 31 and the second rod member 51, each of the positional relationship in the longitudinal direction and the positional relationship about the longitudinal axis C (rotation direction) can be separately adjusted.

Therefore, according to the configuration of the present embodiment, in comparison to the case of joining the first rod member and the second rod member by screw fastening, positioning can be easily performed between the first rod member 31 and the second rod member 51. Therefore, in comparison to the case of joining the first rod member and the second rod member by screw fastening, dimensional errors caused by components can be easily absorbed.

In the present embodiment, when joining the first rod member 31 and the second rod member 51, a compressed surface pressure Pm acting in a radial direction is used. Here, the stress Pv caused by the ultrasonic vibration, which is a longitudinal vibration, acting on the vibration transmitter 8, is a compressive stress or a tensile stress, therefore acts in a longitudinal direction (a vibration direction of the longitudinal vibration), and hardly acts in a radial direction (a direction intersecting with the longitudinal vibration). Therefore, in the present embodiment, by using the compressed surface pressure Pm in a direction in which the stress caused by the ultrasonic vibration does not act in the vibration transmitter 8, the first rod member 31 and the second rod member 51 can be joined efficiently. The transmissibility of the ultrasonic vibration is also improved between the first rod member 31 and the second rod member 51.

Furthermore, in the case where the members are joined by screw fastening, a thread is formed on the inner circumferential surface of the fitting hole of the first rod member and on the outer circumferential surface of the fitting portion of the second rod member to allow threadable attachment to each other, and the surfaces thereof are formed unevenly. In this case, at a portion where the fitting hole and the fitting portion come in contact, for example, the direction and the magnitude of the joining stress, such as the compressed surface pressure, may vary depending on the position. In the present embodiment, the first rod member 31 and the second rod member 51 are joined by the shrinkage fitting or the pressing fitting. Therefore, the inner circumferential surface 37 of the fitting hole 35 of the first rod member 31 and the outer circumferential surface 56 of the fitting portion 55 of the second rod member 51 are formed smoothly and are not unevenly shaped. Therefore, in comparison to the case of joining the first rod member and the second rod member by the screw fastening, the direction and the magnitude of the compressed surface pressure Pm are made even, and the change according to the position of the compressed surface pressure Pm is made smaller.

Furthermore, the joining strength S between the first rod member 31 and the second rod member 51 is made higher than the threshold value Sth. In the present embodiment, a maximum value of the torque acting on the vibration transmitter 8 in the surgical procedure using the treatment device 1 is used for the threshold value Sth. Therefore, since the joining strength S is higher than the threshold value Sth, the fitting of the second rod member 51 to the first rod member 31 can be maintained more reliably, thereby ensuring the treatment device 1 to be used safely in the procedure.

Furthermore, at the distal end treatment portion 23 of the vibration transmitter 8, a vibration velocity V of the ultrasonic vibration becomes larger than that at the proximal part. Therefore, the second rod member 51 including the distal end treatment portion 23 is preferably formed of a material of higher strength than that of the first rod member 31. In the present embodiment, the second rod member 51 is formed of a titanium alloy, which is a material of higher strength than an aluminum alloy of which the first rod member 31 is formed.

In the present embodiment, the fitting region 29 is positioned in the vicinity of the antinode position Aj, which is the antinode of vibration. In the vicinity of the antinode position Aj, the stress Pv caused by the ultrasonic vibration acting on the vibration transmitter 8 becomes smaller. Therefore, by forming the fitting region 29 in the vicinity of the antinode position Aj, the first rod member 31 and the second rod member 51 can be joined at a portion where the stress Pv caused by the ultrasonic vibration is small. In addition, in the vicinity of the antinode position Aj, the displacement of ultrasonic vibration in the radial direction becomes smaller, making the fluctuation of the interference Δd smaller. As a result, the fluctuation of the compressed surface pressure Pm becomes smaller in the vicinity of the antinode position Aj. This suppresses slippage at the joint between the first rod member 31 and the second rod member 51, and further improves the transmissibility of the ultrasonic vibration.

In the present embodiment, the fitting region 29 exists on the proximal side of the antinode position Aj, which is the antinode of vibration. Therefore, in the fitting region 29, the stress Pv acting on the vibration transmitter 8 and the displacement in the radial direction caused by the ultrasonic vibration increase from the distal side toward the proximal side, that is, from the antinode position Aj toward the node position Nj. Furthermore, in the fitting region 29, the compressed surface pressure Pm acting on the second rod member 51 increases from the distal side toward the proximal side. Therefore, in the present embodiment, as the stress Pv acting on the vibration transmitter 8 and the displacement in the radial direction caused by the ultrasonic vibration increase, the compressed surface pressure Pm acting on the second rod member 51 increases in the fitting region 29. At a portion where the stress Pv and the displacement in the radial direction caused by the ultrasonic vibration are large, by increasing the compressed surface pressure Pm, the slippage at the joint between the first rod member 31 and the second rod member 51 in the fitting region 29 is suppressed, thereby further increasing transmissibility of the ultrasonic vibration.

Furthermore, in a case where the first rod member 31 and the second rod member 51 are joined by the shrinkage fitting, the strength becomes lower in the fitting region 29 than in the non-fitting region 30. In the present embodiment, by disposing the fitting region 29 in the vicinity of the antinode of vibration, the stress Pv acting on the vibration transmitter 8 becomes smaller in the fitting region 29 than in the case where the fitting region 29 is disposed in the vicinity of the node of vibration. Therefore, by disposing a portion where the stress Pv becomes small in a portion where the strength becomes low, damage to the member caused by excessive stress can be prevented.

Furthermore, in the case where the first rod member 31 and the second rod member 51 are joined by the shrinkage fitting, the crystal becomes coarser and the crystal grain diameter becomes larger in the fitting region 29 than in the non-fitting region 30. Here, in a portion where the crystal is coarsened, the generation of unintended vibrations such as the generation of transverse vibration is suppressed. Furthermore, unintended vibration such as the transverse vibration is considered to be generated more easily at the antinode position of vibration than at the node position of vibration. In the present embodiment, the fitting region 29 is positioned in the vicinity of the antinode position Aj. Therefore, by providing a portion in which the unintended vibration is easily generated at a portion in which the generation of unintended vibration is suppressed, the generation of unintended vibration is suppressed effectively, and the transmissibility of the ultrasonic vibration is further improved.

Furthermore, in the fitting hole 35, the stress Pv may increase due to stress concentration at a corner portion or a curved portion between the bottom surface 36 and the inner circumferential surface 37. In the present embodiment, the bottom surface 36 is positioned at a position away from the node position Nj. Therefore, in the present embodiment, by providing the bottom surface 36 at a position away from the node position Nj, in comparison to a case in which the bottom surface 36 is provided at the node position Nj, the portion at which the stress concentration occurs is disposed at a portion where the stress Pv is smaller. This effectively reduces the influence of the stress concentration between the bottom surface 36 and the inner circumferential surface 37.

Furthermore, in the present embodiment, the fitting portion 55 is the maximum outer diameter portion 27 in the second rod member 51. Therefore, when manufacturing the second rod member 51, the cutting amount when forming the fitting portion 55 can be reduced. As a result, the manufacturing cost of the second rod member 51 can be further reduced.

In the present embodiment, the ultrasonic vibration transmitted to the vibration transmitter 8 is a longitudinal vibration that is displaced along the longitudinal axis. In the transmission of the longitudinal vibration, when the outer diameter of the vibration transmitter 8 becomes larger than $\lambda/4$, an unintended vibration such as a transverse vibration is likely to be generated. In the present embodiment, the outer diameter D of the second rod member 51 in the fitting region 29 is formed equal to or smaller than $\lambda/4$. Therefore, in the fitting region 29, the generation of the transverse vibration is effectively suppressed, and the influence of the generation of the transverse vibration is reduced.

The above embodiment can be modified as will be explained with reference to FIG. 5. The same reference numerals will be assigned to the elements identical to those in the above embodiment, and the description of such elements will be omitted.

Figure 5:
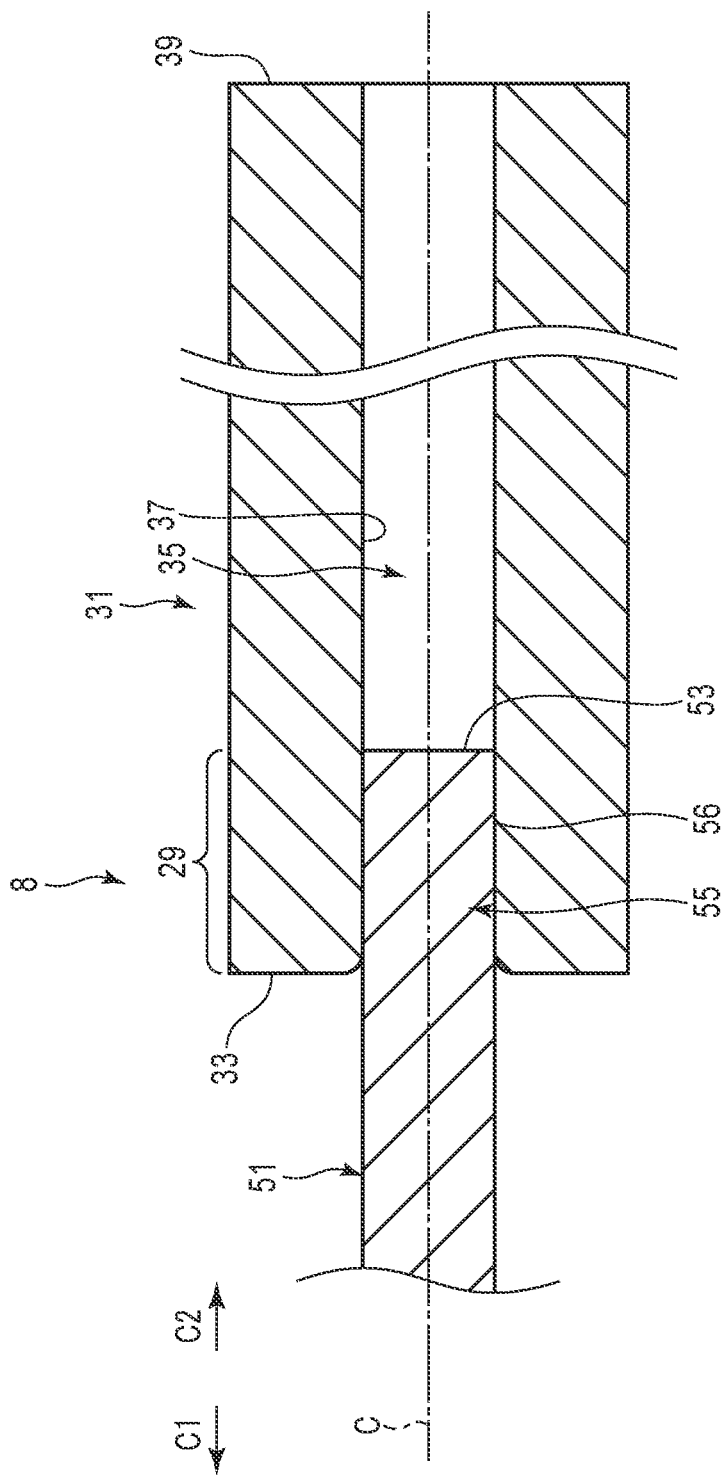
FIG. 5 is a schematic view showing a configuration of a fitting portion between a first rod member and a second rod member in a cross section taken along a longitudinal axis in a vibration transmitter according to an exemplary embodiment.

As shown in FIG. 5, the above embodiment can be modified by forming a fitting hole 35 along a longitudinal axis C over a range from a distal surface 33 to a proximal surface 39 of a first rod member 31. That is, the fitting hole 35 penetrates the first rod member 31 in a longitudinal direction. The fitting hole 35 is formed in substantially the same shape across the entire length of the longitudinal direction.

In the present example, the fitting hole 35 is formed in substantially the same shape across the entire length of the first rod member 31 along the longitudinal direction. Therefore, in the fitting hole 35, a portion at which stress concentration occurs, such as a corner portion or a curved surface, is not formed. Therefore, the occurrence of the stress concentration is suppressed in the fitting hole 35.

Another modification of the above embodiment will be explained with reference to FIG. 6. The same reference numerals will be assigned to the elements identical to those in the above embodiment, and the description of such elements will be omitted.

Figure 6:
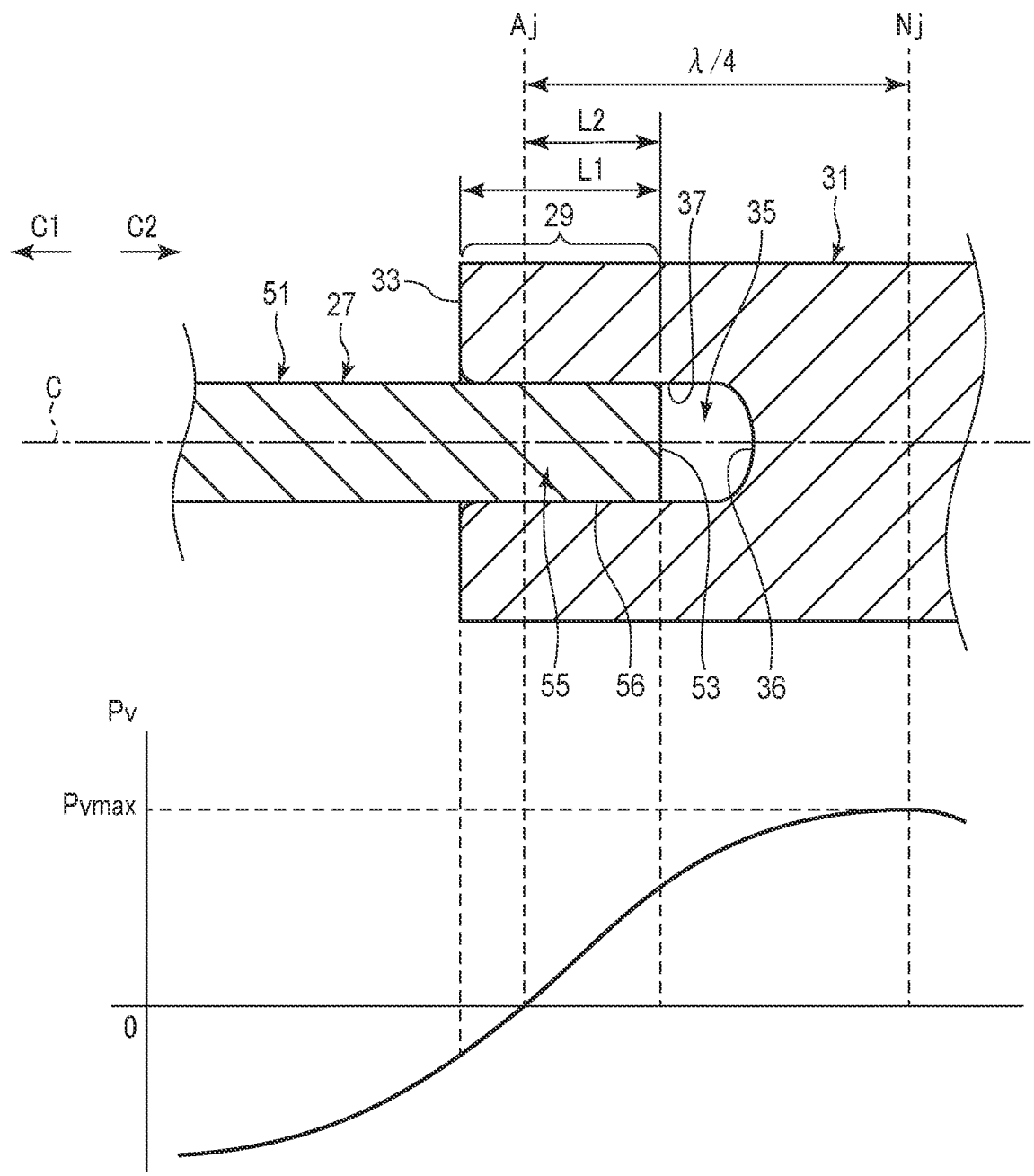
FIG. 6 is a schematic view showing a configuration of a fitting portion between a first rod member and a second rod member, and distribution of stress caused by vibration in a longitudinal direction in a cross section taken along a longitudinal axis in a vibration transmitter according to an exemplary embodiment.

As shown in FIG. 6, in the present example, an antinode position Aj closest to a fitting region 29 is positioned between a distal surface 33 of a first rod member 31 and a proximal surface 53 of a second rod member 51. That is, the antinode position Aj is positioned within the range of the fitting region 29. Furthermore, also in the present modification, each of the proximal surface 53 of the second rod member 51 and a bottom surface 36 of a fitting hole 35 is positioned on the distal side of a node position Nj between the antinode position Aj and a node position Nj. Therefore, a distance L2 between the antinode position Aj and the proximal surface 53 of the second rod member 51 becomes smaller than $\lambda/4$.

Inside the fitting region 29, the force of a stress Pv caused by ultrasonic vibration acts in opposite directions between the proximal side of the antinode position Aj and the distal side of the antinode position Aj. For example, on the proximal side of the antinode position Aj in the fitting region 29, the stress Pv becomes a compressive stress, and, on the distal side of the antinode position Aj in the fitting region 29, the stress Pv becomes a tensile stress.

In the present modification, the antinode position Aj is positioned inside the fitting region 29. Therefore, the first rod member 31 and the second rod member 51 are joined at the outer circumference of a position including the antinode of vibration. In the vicinity of the antinode of vibration, the stress Pv caused by the vibration acting on a vibration transmitter 8 becomes small. Therefore, by joining the first rod member 31 and the second rod member 51 at a portion where the stress Pv caused by the vibration is small, the vibration transmissibility between the first rod member 31 and the second rod member 51 improves.

In the present modification, in the fitting region 29, the stress Pv in two directions that are opposite each other in the longitudinal direction acts on the vibration transmitter 8. Therefore, in the fitting region 29, the compressive stress and the tensile stress both act on the vibration transmitter 8. When considering the balance of force in the longitudinal direction over the entire range of the fitting region 29, the force in the longitudinal direction applied to the entire fitting region 29 decreases as a result of the differences between the compressive stress and the tensile stress. Therefore, when both the compressive stress and the tensile stress act on the vibration transmitter 8 in the fitting region 29, it is more unlikely that the first rod member 31 and the second rod member 51 become disjoined compared to a case in which only one of the compressive stress or the tensile stress acts on the vibration transmitter 8. That is, in the present modification, when the stress caused by the ultrasonic vibration acts on the vibration transmitter 8 from both sides of the longitudinal direction in the fitting region 29, the first rod member 31 and the second rod member 51 become difficult to be disjoined.

Another modification of the above embodiment will be described with reference to FIG. 7. The same reference numerals will be assigned to the elements identical to those in the above embodiment, and the description of such elements will be omitted.

Figure 7:
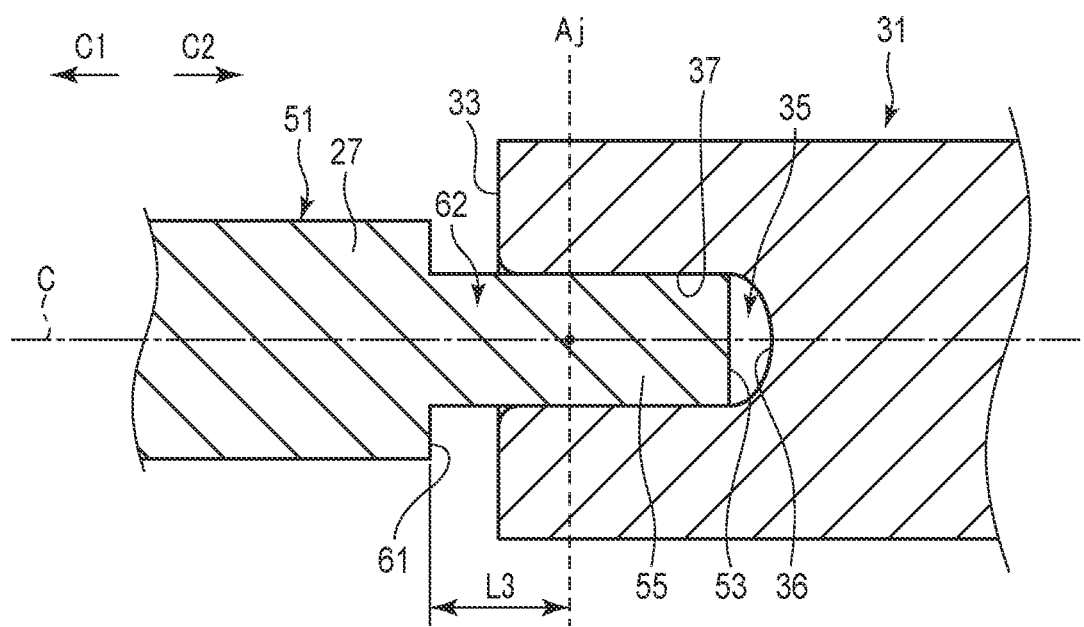
FIG. 7 is a schematic view showing a configuration of a fitting portion between a first rod member and a second rod member in a cross section taken along a longitudinal axis in a vibration transmitter according to an exemplary embodiment.

As shown in FIG. 7, in the present example, a fitting portion 55 of a second rod member 51 is formed by a part of a projecting portion 62 extending from a proximal end 61 of a maximum outer diameter portion 27 to the proximal side. The projecting portion 62 is formed thinner than the maximum outer diameter portion 27 and has a smaller outer diameter than the maximum outer diameter portion 27. The outer diameter of the projecting portion 62 is substantially the same as an inner diameter of a fitting hole 35 of a first rod member 31 in a state where it is fitted into a fitting hole 35. In the present modification, a proximal part of the projecting portion 62 is the fitting portion 55 and is fitted into the fitting hole 35.

The projecting portion 62 is provided over a range from a proximal surface 53 to the proximal end 61 of the maximum outer diameter portion 27 in a longitudinal direction. The proximal end 61 of the maximum outer diameter portion 27 is positioned on the distal side of a distal surface 33 of the first rod member 31. A distance L3 between the proximal end 61 of the maximum outer diameter portion 27 and an antinode position Aj is equal to or shorter than a wavelength (equal to or smaller than $\lambda$). Furthermore, the proximal end 61 of the maximum outer diameter portion 27 is positioned within a range at which a distance from the distal surface 33 of the first rod member 31 becomes equal to or shorter than a wavelength (equal to or smaller than $\lambda$) of a vibration. That is, the proximal end 61 of the maximum outer diameter portion 27 is positioned within a range at which a distance from a fitting region 29 becomes equal to or smaller than a wavelength (equal to or smaller than $\lambda$) of a vibration.

When manufacturing the second rod member 51, the projecting portion 62 is formed by cutting, for example, a material of substantially the same diameter as that of the maximum outer diameter portion 27. Therefore, the projecting portion 62 preferably has a length (extended length) as short as possible in the longitudinal direction. That is, it is preferable to position the proximal end 61 of the maximum outer diameter portion 27, which is to be the distal position of the projecting portion 62, on the proximal side to the extent possible. By forming the extended length of the projecting portion 62 as short as possible, the cutting amount when forming the projecting portion 62 can be reduced. Thus, the manufacturing cost of the second rod member 51 can be reduced.

Another modification of the above embodiment will be described with reference to FIG. 8. The same reference numerals will be assigned to the elements identical to those in the above embodiment, and the description of such elements will be omitted.

Figure 8:
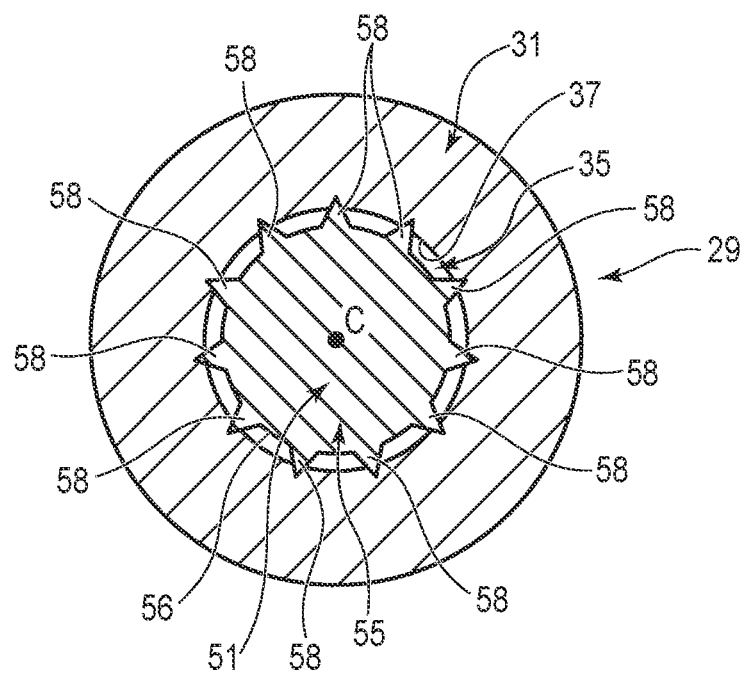
FIG. 8 is a cross-sectional view taken along the line X-X of FIG. 2 according to an exemplary embodiment.

FIG. 8 shows a cross-sectional view of a first rod member 31 and a second rod member 51 in a fitting region 29 in the present modification. As shown in FIG. 8, the second rod member 51 includes a plurality of convex portions (fitting projections) 58 provided on an outer circumferential surface 56 of a fitting portion 55. The convex portions 58 project outward in a radial direction from the outer circumferential surface 56. Each of the convex portions 58 is extended along a longitudinal direction. The convex portions 58 are arranged side by side about a longitudinal axis C. The convex portions 58 are formed, for example, by blast processing. By forming the convex portions 58 by blast processing, the hardness of the convex portions 58 improves. The projecting length of the convex portions 58 from the outer circumferential surface 56 is, for example, 0.5 mm or less.

In a state where the first rod member 31 and the second rod member 51 are joined, the convex portions 58 are fitted into an inner circumferential surface 37 of a fitting hole 35 in a state where they are sunk into the inner circumferential surface 37 by a compressed surface pressure Pm from the inner circumferential surface 37 of the fitting hole 35 of the first rod member 31 to the outer circumferential surface 56 of the fitting portion 55 of the second rod member 51. When the projecting portions 58 are fitted into the inner circumferential surface 37, the movement of the fitting portion 55 with respect to the fitting hole 35 is restricted, thereby strengthening the joint between the first rod member 31 and the second rod member 51. The first rod member 31 is preferably formed of a material having a lower strength than the second rod member 51.

The fitting projections 58 may also be provided on the inner circumferential surface 37 of the fitting hole 35 of the first rod member 31.

Another modification of the present embodiment will be described with reference to FIG. 9. The same reference numerals will be assigned to the elements identical to those in the above embodiment, and the description of such elements will be omitted.

Figure 9:
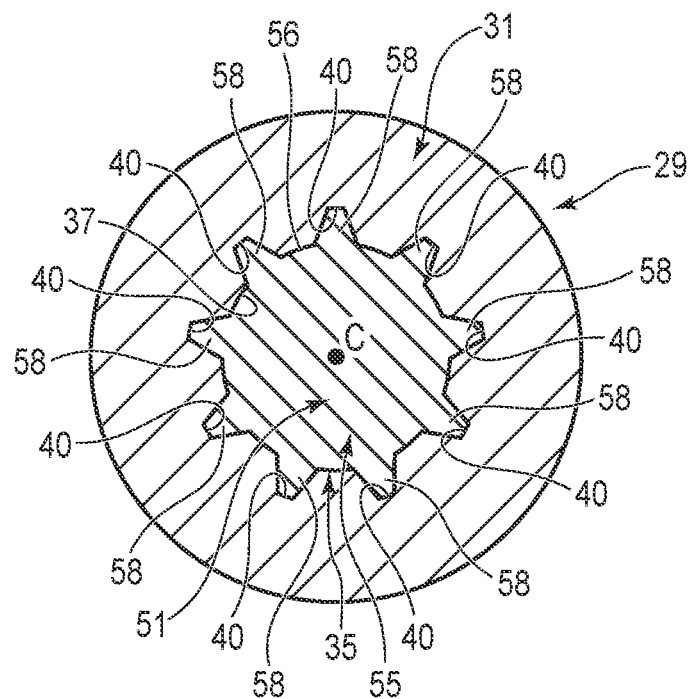
FIG. 9 is a cross-sectional view taken along the line X-X of FIG. 2 according to an exemplary embodiment.

FIG. 9 shows a cross-sectional view of a first rod member 31 and a second rod member 51 in a fitting region 29 in the present modification. As shown in FIG. 9, an outer circumferential surface 56 of a fitting portion 55 of the second rod member 51 is provided with a plurality of convex portions (fitting projections) 58 in the same manner discussed above with respect to the example shown in FIG. 8.

In the present example, the first rod member 31 includes a plurality of concave portions (fitting grooves) 40 provided on an inner circumferential surface 37 of a fitting hole 35. The concave portions 40 are grooves that are concaved inwardly from the inner circumferential surface 37 in a radial direction. Each of the concave portions 40 is extended along a longitudinal direction. The concave portions 40 are arranged side by side about a longitudinal axis C. The concave portions 40 are provided as many as the number of the convex portions 58 of the second rod member 51.

To each of the concave portions 40, one corresponding convex portion 58 among the convex portions 58 is fitted. When the concave portion 40 corresponding to the convex portion 58 is fitted, the movement of the fitting portion 55 with respect to the fitting hole 35 is further restricted, thereby strengthening the joint between the first rod member 31 and the second rod member 51.

In the present modification, the fitting grooves 40 are provided on the inner circumferential surface 37 of the fitting hole 35 of the first rod member 31, and the fitting projections 58 are provided on the outer circumferential surface 56 of the fitting portion 55 of the second rod member 51; however, this is not a limitation. The fitting projections may be provided on the inner circumferential surface 37 of the fitting hole 35 of the first rod member 31, and the fitting grooves may be provided on the outer circumferential surface 56 of the fitting portion 55 of the second rod member 51.

Another exemplary embodiment will be described with reference to FIG. 10. In the present embodiment, the configuration of the above embodiment is modified in the following manner. The same reference numerals will be assigned to the elements identical to those in the above embodiment, and the description of such elements will be omitted.

Figure 10:
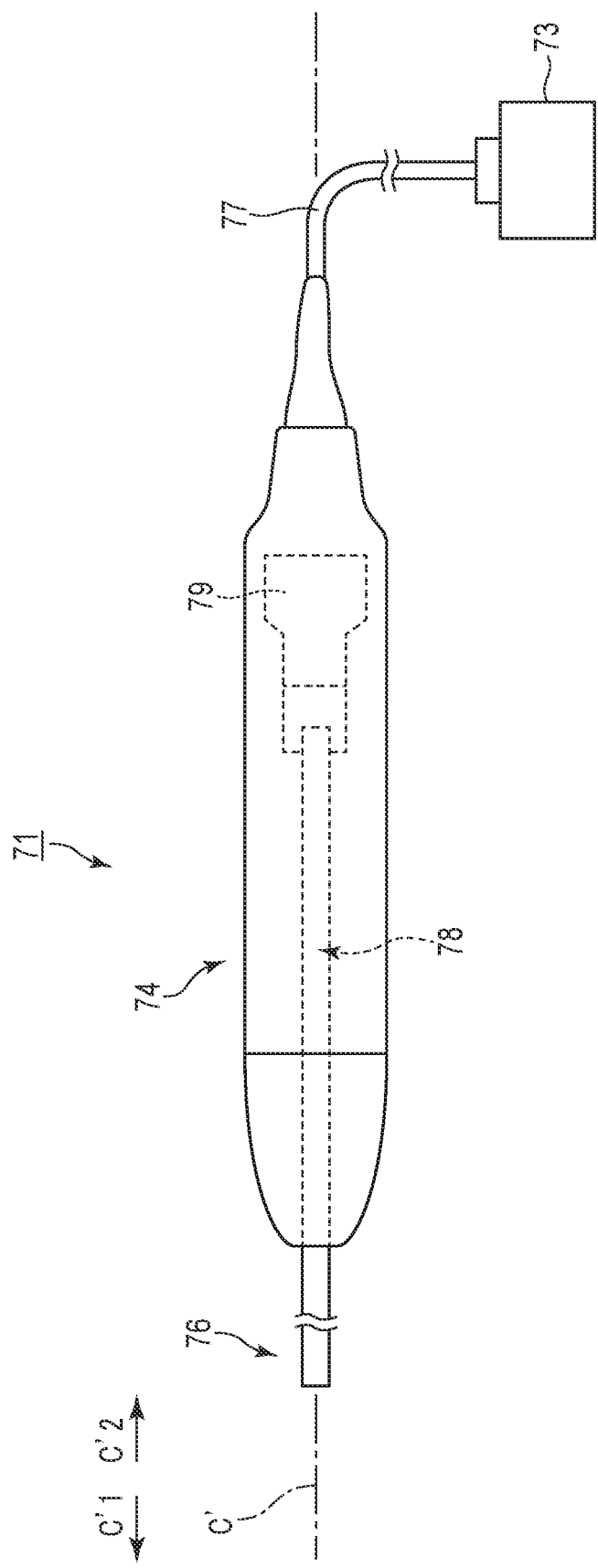
FIG. 10 is a schematic diagram showing an ultrasonic treatment device according to an exemplary embodiment.

FIG. 10 shows a treatment device 71, which is an ultrasonic treatment device according to the present embodiment. The treatment device 71 of the present embodiment is used in a surgical procedure for treating a bone, etc. under an arthroscope. In this procedure, the bone is trimmed and/or punctured by contacting the bone with, for example, a treatment portion to which ultrasonic vibrations are transmitted.

As shown in FIG. 10, the treatment device 71 includes a housing 74 that can be held. One end of a cable 77 is connected to the housing 74. The other end of the cable 77 is detachably connected to a power source device 73.

The housing 74 defines a longitudinal axis C'. Here, the direction along the longitudinal axis C' is set as a longitudinal direction. One side of the longitudinal direction will be referred to as a distal side (an arrow C'1 side of FIG. 10), and the opposite side of the distal side will be referred to as a proximal side (an arrow C'2 side of FIG. 10). The housing 74 extends along the longitudinal axis C' from the proximal side to the distal side.

Inside the housing 74, an ultrasonic transducer 79 and a vibration transmitter (ultrasonic probe) 78 that is connected to the ultrasonic transducer 79 from the distal side thereof are provided. The vibration transmitter (ultrasonic probe) 78 extends along the longitudinal axis C'. A distal part of the vibration transmitter 78 projects from the distal end of the housing 74 toward the distal side. A projecting portion of the vibration transmitter 78 from the housing 74 forms an end effector 76 for treating a treatment target.

The configuration of the vibration transmitter 8 according to the above exemplary embodiments, including the various exemplary modifications thereof may also be applied to the vibration transmitter 78 used in the treatment device 71 of the present embodiment. Since the vibration transmitter 78 has the same configuration as the vibration transmitter 8, the treatment device 71 of the present embodiment has the same effect as the treatment device 1 according to the above exemplary embodiment and each of the exemplary modifications thereof.

All of the embodiments disclosed herein share the following common features. An ultrasonic treatment device (1:71) includes a first rod member (31) including a distal end (33) and a proximal end (39), extending along a longitudinal axis (C:C'), including a fitting hole (35) extending along the longitudinal axis (C:C') from the distal end (33) toward a proximal side, and to which a transducer (9:79) for generating ultrasonic vibration can be connected on a proximal part thereof, and a second rod member (51) extending along the longitudinal axis (C:C'), attached to a distal side of the first rod member (31), and including a fitting portion (55) to be fitted into the fitting hole (35) in a state where a compressed surface pressure (Pm) is received from an inner circumferential surface (37) of the fitting hole (35), and includes a vibration transmitter (8:78) capable of transmitting vibration of a predetermined resonance frequency (f) generated at the transducer (9:79) from a proximal part of the first rod member (31) to a distal end of the second rod member (51) along the longitudinal axis (C:C'), in which, in a state where the vibration transmitter (8:78) vibrates at the predetermined resonance frequency (f), an antinode (Aj) of vibration closest to a proximal end (53) of the second rod member (51) is positioned more on a distal side than the proximal end (53) of the second rod member (51).

Note that the present disclosure is not limited to the above embodiments, and can be modified in various ways without departing from the gist of the present disclosure in the implementation stage. Furthermore, each embodiment may be implemented by appropriate combinations thereof to a maximum extent; in which case a combined effect will be obtained. Moreover, the above embodiments include various stages, and various embodiments may be extracted by appropriate combinations of a plurality of disclosed configuration requirements.

The invention claimed is:

1. A vibration transmitter comprising:
a first rod that extends along a longitudinal axis from a distal end to a proximal end, and includes a fitting hole extending along the longitudinal axis from the distal end toward the proximal end; and
a second rod member that extends along the longitudinal axis, is attached to a distal end portion of the first rod, and includes a fitting portion fitted into the fitting hole in a state where a compressed surface pressure is received from an inner surface of the fitting hole, wherein:
the first rod includes:
a first region in which the fitting portion is fitted into the fitting hole; and
a second region positioned proximal of the first region, and
a crystal grain diameter in the first region of the first rod is larger than a crystal grain diameter in the second region of the first rod.

2. The vibration transmitter according to claim 1, wherein:
the second rod includes a first region in which the fitting portion is fitted into the fitting hole, and a second region positioned distal of the first region, and
a crystal grain diameter in the first region of the second rod is larger than a crystal grain diameter in the second region of the second rod.

3. The vibration transmitter according to claim 1, wherein:
the first rod includes a first index defining a reference position, and
the second rod includes a second index defining a positional relationship with respect to the first index.

4. The vibration transmitter according to claim 3, wherein:
the first index is a first reference surface, and
the second index is a second reference surface defining a positional relationship about the longitudinal axis with respect to the first reference surface of the first index.

5. The vibration transmitter according to claim 3, wherein the second index defines a positional relationship with respect to the first index relative to a direction along the longitudinal axis.

6. The vibration transmitter according to claim 1, wherein the fitting hole penetrates the first rod along the longitudinal axis.

7. The vibration transmitter according to claim 1, wherein:
the first rod is formed of an aluminum alloy, and
the second rod is formed of a titanium alloy.

8. The vibration transmitter according to claim 1, wherein the fitting portion includes a projection projecting outward in a radial direction from an outer circumferential surface of the fitting portion.

9. The vibration transmitter according to claim 1, wherein the second rod is made of a material that has a higher strength than a material of the first rod.

10. The vibration transmitter according to claim 1, wherein the inner surface of the fitting hole includes a plurality of concave portions.

11. An ultrasonic treatment device comprising:
a transducer configured to generate ultrasonic vibration;
a housing in which the transducer is provided; and
a vibration transmitter comprising:
   a first rod that extends along a longitudinal axis from a distal end to a proximal end, and includes a fitting hole extending along the longitudinal axis from the distal end toward the proximal end; and
   a second rod that extends along the longitudinal axis, is attached to a distal end portion of the first rod, and includes a fitting portion fitted into the fitting hole in a state where a compressed surface pressure is received from an inner surface of the fitting hole, the vibration transmitter being capable of transmitting vibration of a predetermined resonance frequency generated by the transducer from a proximal part of the first rod to a distal end of the second rod along the longitudinal axis, wherein:
in a state where the vibration transmitter vibrates at the predetermined resonance frequency, an antinode of vibration closest to a proximal end of the second rod is positioned distal of the proximal end of the second rod,
the first rod includes a first region in which the fitting portion is fitted into the fitting hole, and a second region positioned proximal of the first region, and
a crystal grain diameter in the first region of the first rod is larger than a crystal grain diameter in the second region of the first rod.

12. The ultrasonic treatment device according to claim 11, wherein:
the second rod includes a maximum cross-sectional area portion having a cross-sectional area extending in a direction orthogonal to the longitudinal axis that is a largest cross-sectional area in the second rod, and
the maximum cross-section area portion is distal of the antinode of vibration closest to the proximal end of the second rod, and a distance between at least a part of the maximum cross-sectional area portion and the antinode of vibration closest to the proximal end of the second rod is equal to or shorter than one wavelength of the vibration.

13. The ultrasonic treatment device according to claim 11, wherein a length of the fitting portion in a direction along the longitudinal axis is equal to or shorter than ¼ of a wavelength of the vibration.

14. The ultrasonic treatment device according to claim 11, wherein:
an end surface of the fitting hole facing the proximal end of the second rod is positioned proximal of the antinode of vibration closest to the proximal end of the second rod, and
a distance between the end surface of the fitting hole and the antinode of vibration is equal to or shorter than ¼ of a wavelength of the vibration.

15. The ultrasonic treatment device according to claim 11, wherein a ratio of a vibration velocity of the vibration with respect to the compressed surface pressure is equal to or smaller than 0.176.

16. The ultrasonic treatment device according to claim 11, wherein a joining strength between the first rod and the second rod is higher than a torque to be added to the ultrasonic treatment device.

17. The ultrasonic treatment device according to claim 11, wherein in a state where the vibration transmitter vibrates at the predetermined resonance frequency, an antinode of vibration closest to a proximal end of the second rod is positioned proximal of the distal end of the first rod.

* * * * *